United States Patent
Beeson

(10) Patent No.: US 8,663,996 B2
(45) Date of Patent: Mar. 4, 2014

(54) DETERMINING OXYGEN CONCENTRATION IN ULLAGE USING CATALYTIC OXIDATION

(75) Inventor: William Beeson, West Hartford, CT (US)

(73) Assignee: Hamilton Sundstrand Corporation, Windsor Locks, CT (US)

(*) Notice: Subject to any disclaimer, the term of this patent is extended or adjusted under 35 U.S.C. 154(b) by 778 days.

(21) Appl. No.: 12/767,384

(22) Filed: Apr. 26, 2010

(65) Prior Publication Data
US 2011/0263035 A1  Oct. 27, 2011

(51) Int. Cl.
*G01N 33/00* (2006.01)
*B01J 19/00* (2006.01)

(52) U.S. Cl.
USPC ........... 436/138; 436/136; 436/127; 422/119; 422/111; 422/110; 422/108; 422/105

(58) Field of Classification Search
USPC .......... 436/138, 136, 127; 422/119, 111, 110, 422/108, 105
See application file for complete search history.

(56) References Cited

U.S. PATENT DOCUMENTS

| | | |
|---|---|---|
| 3,847,298 A | 11/1974 | Hamilton |
| 4,378,920 A | 4/1983 | Runnels et al. |
| 4,556,180 A | 12/1985 | Manatt |
| 4,681,602 A | 7/1987 | Glenn et al. |
| 4,795,090 A | 1/1989 | Koukal et al. |
| 5,069,692 A | 12/1991 | Grennan et al. |
| 5,131,225 A | 7/1992 | Roettger |
| 6,314,754 B1 | 11/2001 | Kotliar |
| 6,401,487 B1 | 6/2002 | Kotliar |
| 6,418,752 B2 | 7/2002 | Kotliar |
| 6,502,421 B2 | 1/2003 | Kotliar |
| 6,557,374 B2 | 5/2003 | Kotliar |
| 6,560,991 B1 | 5/2003 | Kotliar |
| 6,585,192 B2 | 7/2003 | Beers |
| 6,634,598 B2 | 10/2003 | Susko |
| 6,729,359 B2 | 5/2004 | Jones |
| 6,739,359 B2 | 5/2004 | Jones et al. |
| 6,904,930 B2 | 6/2005 | Susko |
| 6,913,636 B2 | 7/2005 | Defrancesco et al. |
| 7,013,905 B2 | 3/2006 | Jones et al. |
| 7,081,153 B2 | 7/2006 | Leigh et al. |

(Continued)

FOREIGN PATENT DOCUMENTS

| | | |
|---|---|---|
| WO | WO 00/00389 A2 | 1/2000 |
| WO | WO 02/28714 A1 | 4/2002 |

OTHER PUBLICATIONS

Cavage, William M., Measuring Oxygen Concentration in a Fuel Tank Ullage, American Institute of Aeornautics and Astronautics, Inc.,Feb. 10, 2009, pp. 1-5.*

*Primary Examiner* — Christine T Mui
(74) *Attorney, Agent, or Firm* — Kinney & Lange, P.A.

(57) ABSTRACT

A system for measuring the oxygen concentration of a gas includes a catalytic reactor, first and second temperature sensors and a control unit. The catalytic reactor includes a combustion catalyst that supports the catalytic combustion of hydrocarbon fuel vapor in a gas stream. The first temperature sensor is located upstream of the catalytic reactor for sensing an upstream temperature of the gas stream, and the second temperature sensor is located downstream of the catalytic reactor for sensing a downstream temperature of the gas stream. The control unit compares the upstream temperature and the downstream temperature to determine the oxygen concentration of the gas stream.

14 Claims, 3 Drawing Sheets

(56) References Cited

U.S. PATENT DOCUMENTS

| | | |
|---|---|---|
| 7,273,507 B2 | 9/2007 | Schwalm |
| 7,300,494 B2 | 11/2007 | Schwalm et al. |
| 7,509,968 B2 | 3/2009 | Surawski |
| 2002/0028168 A1 * | 3/2002 | Giacobbe et al. ............. 423/212 |
| 2003/0116679 A1 | 6/2003 | Susko |
| 2004/0035461 A1 | 2/2004 | Susko |
| 2004/0065778 A1 | 4/2004 | Jones |
| 2008/0099618 A1 * | 5/2008 | Zaki et al. ................. 244/135 R |
| 2008/0128048 A1 | 6/2008 | Johnson et al. |

* cited by examiner

DETERMINING OXYGEN CONCENTRATION IN ULLAGE USING CATALYTIC OXIDATION

BACKGROUND

On-board nitrogen generation systems can be used to create an inert environment in various locations on an aircraft, such as in the cargo area or fuel tanks. Nitrogen generation systems can produce nitrogen-enriched air using molecular sieve technology or hollow fiber membrane technology. For example, an air separation module containing a plurality of hollow fiber membranes separates compressed air into a nitrogen-enriched portion and an oxygen-enriched portion. The compressed air source can be compressed RAM air or can be bleed air taken from the compressor section of the aircraft engine. A control unit can control the purity or oxygen concentration of the nitrogen-enriched air. For example, a flow control valve can be located downstream of the air separation module to control the flow of air through the air separation module. A faster flow rate through the air separation module results in the nitrogen-enriched air having a lower purity (higher oxygen concentration).

The nitrogen-enriched air produced by the nitrogen generation system can be directed to the fuel tanks of the aircraft. Nitrogen-enriched air is supplied to the fuel tanks in a sufficient quantity to maintain the oxygen concentration in the fuel tank below a specified amount in order to limit the flammability of the fuel tanks.

Oxygen sensors run at high reference temperatures and thus cannot be used to directly measure the oxygen concentration of the fuel tank because of the risk of ignition. Instead, typically an oxygen sensor is located upstream of the fuel tank to measure the oxygen concentration of the nitrogen-enriched air stream flowing into the fuel tank. The sensed values are used to approximate the actual oxygen concentration of the fuel tank based on established models, and the control unit can adjust the oxygen concentration of the nitrogen-enriched air flow based on this feedback.

SUMMARY

A system for measuring the oxygen concentration of a gas includes a catalytic reactor, first and second temperature sensors and a control unit. The catalytic reactor includes a catalyst that supports the combustion of oxygen. The first temperature sensor is located upstream of the catalytic reactor for sensing an upstream temperature of the gas stream, and the second temperature sensor is located downstream of the catalytic reactor for sensing a downstream temperature of the gas stream. The control unit compares the upstream temperature and the downstream temperature to determine the oxygen concentration of the gas stream.

DETAILED DESCRIPTION

A system for measuring oxygen concentration of a gas stream is described herein. The system can measure the oxygen concentration of gases within a space in which a temperature sensor, such as a thermocouple, cannot be used because of the high reference temperature. For example, the system can be used to determine the oxygen concentration of a fuel tank ullage of an aircraft.

Figure 1:
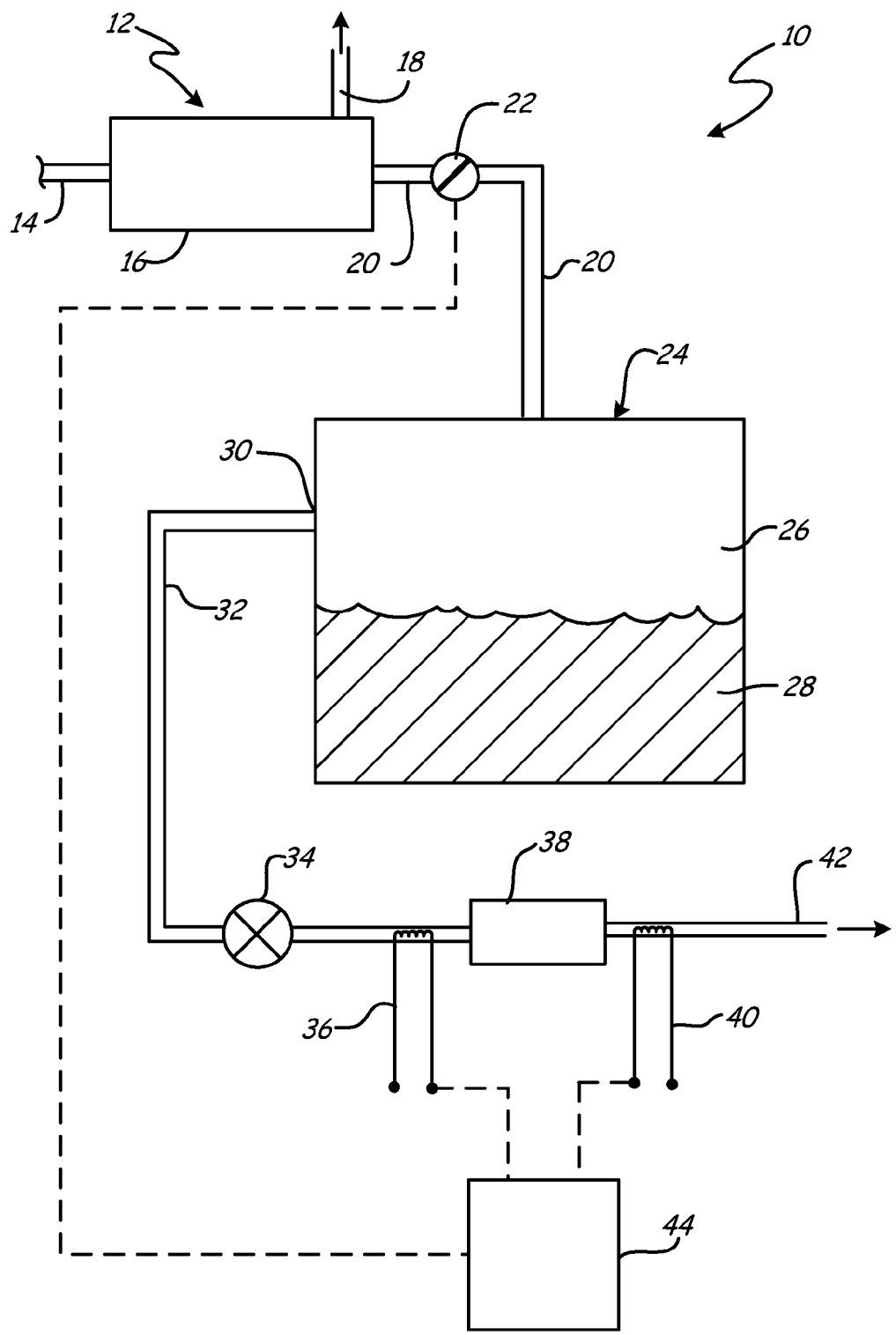
FIG. 1 is a schematic of a fuel tank inerting system having a catalytic reactor.

FIG. 1 is a schematic of a fuel tank inerting system 10, which includes nitrogen generation system (NGS) 12 (having compressed air inlet 14, air separation module 16, oxygen-enriched air line 18, nitrogen-enriched air (NEA) line 20 and NEA flow control valve 22), fuel tank 24 (having ullage portion 26, fuel portion 28 and ullage sample outlet 30), ullage sample line 32, check arrestor 34, upstream temperature sensor 36, catalytic reactor 38, downstream temperature sensor 40, ullage sample outlet 42 and control unit 44. The inlet and outlet through which liquid hydrocarbon fuel flows into and out of fuel tank 24 are not shown.

Nitrogen generation system 12 connects to fuel tank 24 by NEA line 20. Ullage sample line 32 connects fuel tank 24 to check arrestor 34, upstream temperature sensor 36, catalytic reactor 38 and downstream temperature sensor 40, such that a gas sample from ullage portion 26 flows sequentially past check arrestor 34, upstream temperature sensor 36, catalytic reactor 38 and downstream temperature sensor 40.

Nitrogen generation system 12 produces nitrogen-enriched air (NEA) that is supplied through NEA line 20 to fuel tank 24. Nitrogen generation system 12 includes compressed air inlet 14, air separation module 16, oxygen-enriched air line 18, nitrogen-enriched air line 20 and nitrogen-enriched air (NEA) flow control valve 22. Nitrogen generation system 12 may use hollow fiber membrane technology to produce NEA. In an exemplary embodiment, air separation module 16 contains a bundle of hollow fiber membranes. Fast gases, such as oxygen and water, permeate through the hollow fiber membranes while slow gases, such as nitrogen, remain inside the hollow fiber membranes. In this way, air separation module 16 separates compressed air from compressed air inlet 14 into an oxygen-enriched (i.e. nitrogen-depleted) portion and a nitrogen-enriched portion. The oxygen-enriched portion exits air separation module 16 through enriched-oxygen air line 18, and the nitrogen-enriched portion (i.e. NEA) exits air separation module 16 through nitrogen-enriched air line 20.

NEA flow control valve 22 is located downstream of air separation module 16 and controls the purity of the NEA produced by nitrogen generation system 12 by controlling the flow rate through nitrogen generation system 12. The purity of the NEA increases with decreasing flow rate so that decreasing the flow of air through nitrogen generation system 12 (and NEA to fuel tank 24) increases the nitrogen purity (i.e. reduces the oxygen concentration) of the NEA.

The NEA from nitrogen generation system 12 is sent to fuel tank 24 for inerting. Fuel tank 24 includes ullage portion 26 and fuel portion 28. Ullage portion 26 is a gas which can comprise fuel vapor, oxygen, nitrogen and other gaseous components of air. Fuel portion 28 is hydrocarbon fuel which is consumed by the engines of the aircraft. An example hydrocarbon fuel is a kerosene based blend. The NEA from nitrogen-enriched air line 20 decreases the oxygen concentration and the flammability of fuel tank 24. The flammability of fuel tank 24 varies depending on temperature and pressure. Thus, the oxygen concentration that fuel tank 24 must be maintained below to be inert also depends on temperature and pressure.

The oxygen concentration of fuel tank 24 can be determined using catalytic reactor 38. An ullage gas sample of ullage portion 26 is removed through ullage sample outlet 30. The ullage gas sample flows sequentially through ullage sample line 32, check arrestor 34, upstream temperature sensor 36, catalytic reactor 38 and downstream temperature sensor 40 to ullage sample outlet 42. In one example, ullage sample outlet 30 can be a floating valve to prevent the liquid fuel of fuel portion 28 from flowing through ullage sample outlet 30. Check arrestor 34 prevents a flame from burning back into fuel tank 24 and prevents back flow of the ullage gas sample.

Ullage sample line 32 supplies the ullage gas sample to catalytic reactor 38 at a specified flow rate. As described further below, catalytic reactor 38 includes a combustion catalyst which oxidizes the fuel vapor in the presence of oxygen. The catalytic reaction between the fuel vapor, oxygen and combustion catalyst generates heat. Upstream temperature sensor 36 measures the temperature of the ullage gas sample upstream or before catalytic reactor 38, and downstream temperature sensor 40 measures the temperature of the ullage gas sample downstream or after catalytic reactor 38. In one example, upstream temperature sensor 36 and downstream temperature sensor 40 are thermocouples.

Upstream temperature sensor 36 and downstream temperature sensor 40 send a signal representing the respective measurements to control unit 44. Control unit 44 calculates the oxygen concentration of the ullage gas sample based on the temperature difference between upstream temperature sensor 36 and downstream temperature sensor 40. Control unit 44 can adjust at least one parameter of nitrogen generation system 12, such as NEA flow control valve 22, in order to adjust the purity of the NEA sent to fuel tank 24 and thus the oxygen concentration of fuel tank 24.

After flowing past downstream temperature sensor 40, the ullage gas sample exits fuel tank inerting system 10 at ullage sample outlet 42. In one example, the ullage gas sample is dumped overboard. Catalytic reactor 38 enables the oxygen content of fuel tank 24 to be measured without the risk of igniting the fuel vapor.

Figure 2:
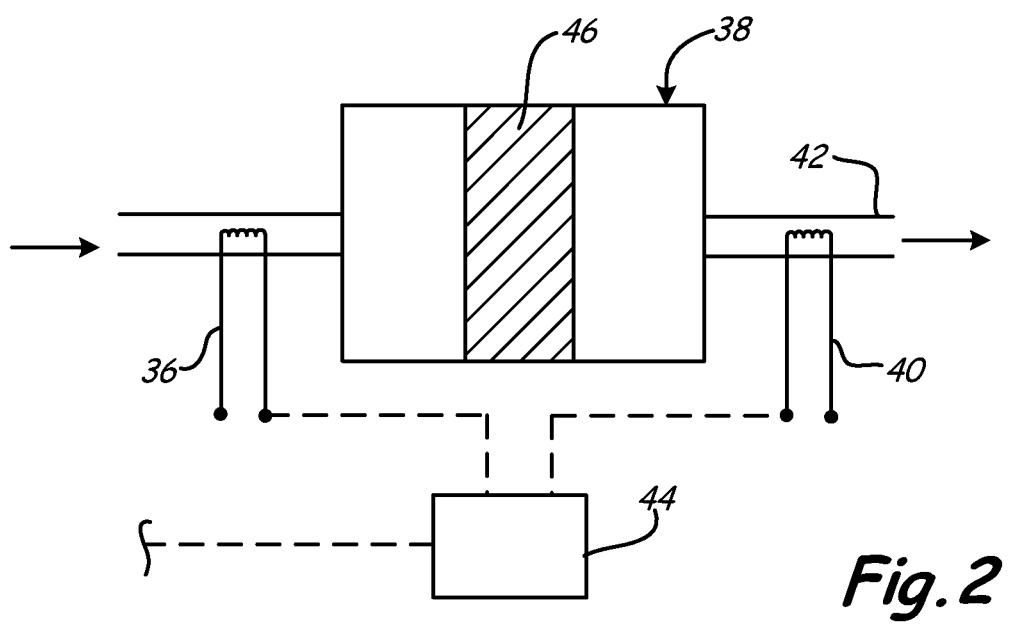
FIG. 2 is an enlarged schematic of the catalytic reactor of FIG. 1.

FIG. 2 is an enlarged schematic view of catalytic reactor 38, which includes combustion catalyst 46. Upstream temperature sensor 36 is positioned upstream of combustion catalyst 46 and downstream temperature sensor 40 is positioned downstream of combustion catalyst 46. Upstream temperature sensor 36 and downstream temperature sensor 40 are connected to control unit 44, enabling control unit 44 to calculate temperature values before and after catalytic reactor 38.

Combustion catalyst 46 can be supported on a substrate, such as a honeycomb structure. Combustion catalyst 46 promotes the catalytic combustion or oxidation of the hydrocarbon fuel vapor in the presence of oxygen. In one example, combustion catalyst 46 includes $Bi_2MoO_6$ or $Pd/Al_2O_3$. If the concentration of fuel vapor and oxygen of the ullage gas sample is high enough, catalytic combustion will occur in catalytic reactor 38, which will generate heat. The heat generated by the catalytic combustion can be calculated by equation (1):

$$\Delta t = t_{out} - t_{in} \qquad (1)$$

Where $t_{out}$ is the temperature measured by downstream temperature sensor 40 and $t_{in}$ is the temperature measured by upstream temperature sensor 36. The rise in temperature can be correlated to laboratory data of flammability and can determine oxygen and fuel vapor content of the ullage gas sample.

For example, the oxygen content of the ullage gas sample can be determined by first calculating the heat flow of the catalytic combustion reaction with equation (2).

$$\dot{Q} = \dot{m} c \Delta t \qquad (2)$$

Where $\dot{Q}$ (Q dot) is the heat energy transfer rate put into (or taken out of) the fuel, $\dot{m}$ (m dot) is the mass flow rate of the ullage gas sample and c is the specific heat capacity of the ullage gas sample. The quantity of fuel combusted is then calculated by dividing the heat energy transfer rate (Q dot) by the heating value (such as the lower heating value) of the hydrocarbon fuel.

Finally, the quantity of oxygen consumed in the catalytic combustion is calculated from the quantity of fuel combusted, the stoichiometric ratio of the hydrocarbon fuel to oxygen of the combustion reaction and the molecular weights of oxygen and the hydrocarbon fuel. The general equation for the catalytic combustion of a hydrocarbon is provided in equation (3).

$$C_xH_y + (x+y/4)O_2 \rightarrow xCO_2 + (y/2)H_2O + \text{energy} \qquad (3)$$

In one example, the ullage gas sample contains excess fuel vapor so that the catalytic combustion is limited by the oxygen of the ullage gas sample and it can be assumed that all oxygen is consumed in the catalytic combustion reaction. In a specific example, the hydrocarbon fuel can be a kerosene based blend primarily consisting of $C_{12}H_{26}$. The mass flow rate of kerosene combusted ($\dot{m}_{kerosene}$) in grams/second is calculated by equation (4).

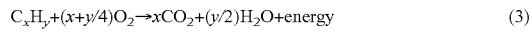

$$\dot{m}_{kerosene} = \dot{m} c \Delta t / LVH_{kerosene} \qquad (4)$$

Where $\dot{m}$ (m dot) is the mass flow rate of the ullage in grams/second, c is the specific heat capacity of the ullage gas sample in Joules/(grams*Kelvin) (approximated as the specific heat capacity of air), $\Delta t$ is the change is temperature across catalytic reactor 38 ($t_{out} - t_{in}$) in Kelvin and $LHV_{kerosene}$ is the low heating value of kerosene (42,000 Joules/gram). The catalytic combustion equation for kerosene is provided in equation (5).

$$C_{12}H_{26}(l) + 37/2 O_2(g) \rightarrow 12CO_2(g) + 13H_2O(g) + \text{energy} \qquad (5)$$

The stoichiometric ratio of kerosene to oxygen is 1 mol kerosene to 37/2 mol oxygen. The molecular weight of kerosene is 170 grams/mol and the molecular weight of oxygen is 32 grams/mol. The mass flow of oxygen ($\dot{m}_{oxygen}$) in grams/second is calculated by equation (6).

$$\dot{m}_{oxygen} = \left( \dot{m}_{kerosene} \times \left( \frac{37}{2} \right) \times 32 \right) / 170 \qquad (6)$$

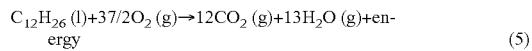

The oxygen concentration of the ullage gas sample can be calculated from the mass flow rate of kerosene and the mass flow rate of oxygen. One skilled in the art will recognize that alternative methods can be used to determine the oxygen concentration of the ullage gas sample from the temperature change across catalytic reactor 38.

Catalytic reactor 38 and upstream and downstream temperature sensors 36 and 40 enable the oxygen content of fuel tank 24 to be determined. Fuel tank inerting system 10 relies on less approximations and more accurately determines the oxygen content of fuel tank 24 compared to previous systems that predicted or estimated the oxygen content of fuel tank 24 based on the oxygen content of the NEA flowing to fuel tank 24. More specifically, control unit 44 compares the temperatures of upstream and downstream temperature sensors 36 and 40 to determine the oxygen concentration of the ullage gas sample and fuel tank 24.

Control unit 44 can control NEA flow control valve 22 based on the determined oxygen content of fuel tank 24 such that fuel tank 24 maintains an inert state. Flammability is a function of temperature and pressure. Fuel tank inerting system 10 enables the nitrogen content of the NEA to be tailored to the specific needs of fuel tank 24 and reduces the amount of excess nitrogen added to fuel tank 24. For example, fuel tank inerting system 10 enables high purity NEA to be sent to fuel tank 24 when control unit 44 determines that fuel tank 24 is not inert and lower purity NEA to be sent to fuel tank 24 when control unit 44 determines that fuel tank 24 has a low oxygen concentration. This results in nitrogen generation system 12 providing only the amount of nitrogen necessary to maintain the inert state of fuel tank 24 and conserves power.

Figure 3:
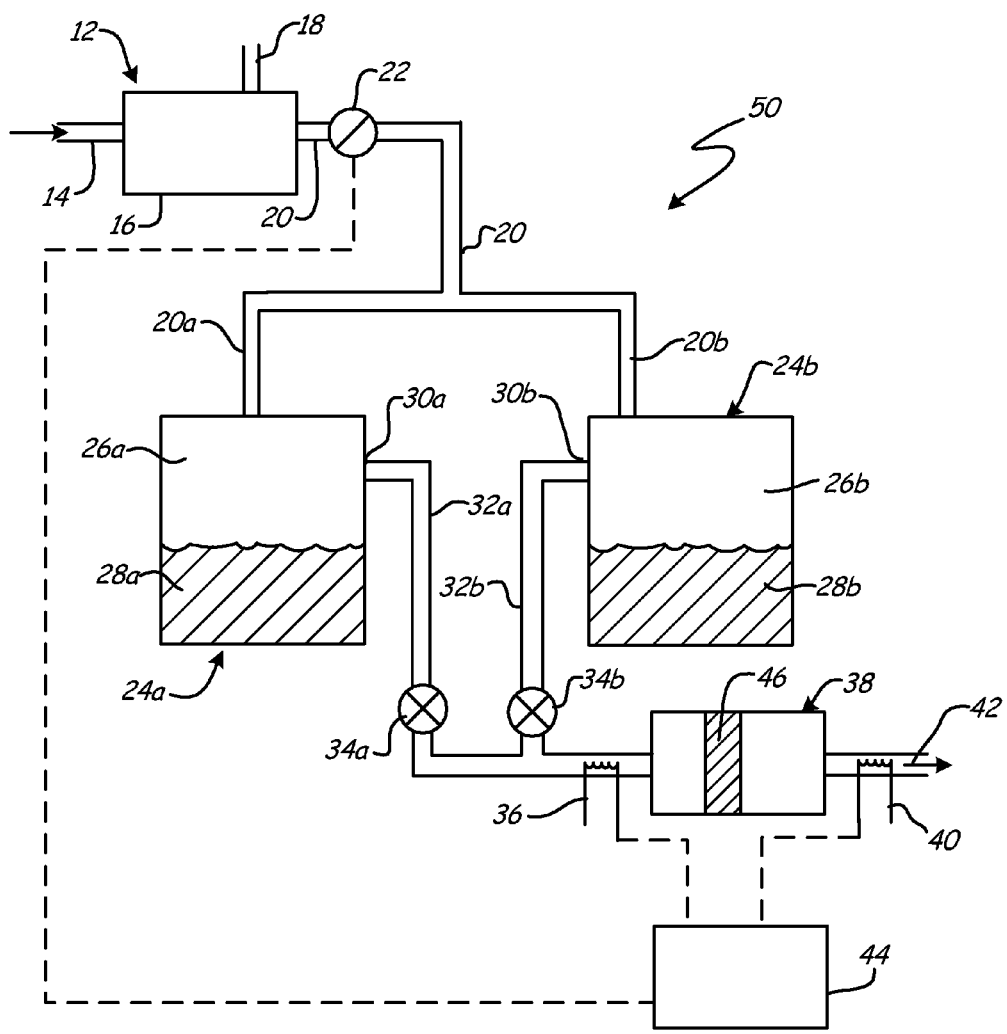
FIG. 3 is a schematic of another fuel tank inerting system having more than one fuel tank and a catalytic reactor.

FIG. 3 illustrates an alternative fuel tank inerting system 50, which includes nitrogen generation system 12, first nitrogen-enriched air line 20a, second nitrogen-enriched air line 20b, first fuel tank 24a (having first ullage portion 26a, first fuel portion 28a and first ullage sample outlet 30a), second fuel tank 24b (having second ullage portion 26b, second fuel portion 28b and second ullage sample outlet 30b). First ullage sample line 32a connects to first check arrestor 34a and second ullage sample line 32b connects to second check arrestor 34b, with flow from both check arrestors 34a and 34b continuing to upstream temperature sensor 36, catalytic reactor 38 (having combustion catalyst 46) and downstream temperature sensor 40.

Similar to fuel tank inerting system 10, compressed air inlet 14 provides compressed air to nitrogen generation system 12. Nitrogen generation system 12 separates the compressed air into an oxygen-enriched portion that exits through oxygen-enriched air line 18 and a nitrogen-enriched portion that exits through nitrogen-enriched air line 20. NEA flow control valve 22 can be modulated to control the purity or oxygen concentration of the nitrogen-enriched air as described above.

Downstream of NEA flow control valve 22, nitrogen-enriched air line 20 splits into first nitrogen-enriched air line 20a and second nitrogen-enriched air line 20b. First nitrogen-enriched air line 20a connects to first fuel tank 24a and second nitrogen-enriched air line 20b connects to second fuel tank 24b. First and second nitrogen-enriched air lines 20a and 20b provide nitrogen-enriched air to first and second fuel tanks 24a and 24b, respectively. NEA flow control valve 22 can be modulated so that the oxygen concentration of first and second fuel tanks 24a and 24b is maintained below a specified value and first and second fuel tanks 24a and 24b are maintained inert.

The oxygen concentration of first fuel tank 24a and the oxygen concentration of second fuel tank 24b are determined using upstream temperature sensor 36, catalytic reactor 38 and downstream temperature sensor 40. An ullage gas sample is removed from first fuel tank 24a through first ullage sample outlet 30a and an ullage gas sample is removed from second fuel tank 24b through second ullage sample outlet 30b. The ullage gas sample from first fuel tank 24a flows through first check arrestor 34a, which prevents a flame from burning back to first fuel tank 24a. Similarly, the ullage gas sample from second fuel tank 24b flows through second check arrestor 34b. After flowing through respective first and second check arrestors 34a and 34b, the ullage gas samples from first and second fuel tanks 24a and 24b are mixed to form a mixed ullage gas sample.

Next, the mixed ullage gas sample flows through upstream temperature sensor 36, catalytic reactor 38 (having combustion catalyst 46) and downstream temperature sensor 40. The mixed ullage gas sample exits through ullage sample outlet 42. Upstream temperature sensor 36 measures the temperature of the mixed ullage gas sample upstream or prior to catalytic reactor 38, and downstream temperature sensor 40 measures the temperature of the mixed ullage gas sample downstream or after catalytic reactor 38. Upstream temperature sensor 36 and downstream temperature sensor 40 are electrically connected to control unit 44. Upstream temperature sensor 36 and downstream temperature sensor 40 provide signals representing the sensed temperatures to control unit 44.

Catalytic reactor 38 is positioned between upstream temperature sensor 36 and downstream temperature sensor 40. Catalytic reactor 38 contains combustion catalyst 46 that supports the catalytic combustion of the hydrocarbon fuel in the presence of oxygen. For example, combustion catalyst 46 can include $Bi_2MoO_6$ or $Pd/Al_2O_3$. Hydrocarbon fuel vapor in the mixed ullage gas sample from first and second fuel tanks 24a and 24b is oxidized by combustion catalyst 46 if enough oxygen is present. This oxidation or catalytic combustion is an exothermic reaction which generates heat. The heat generated by the catalytic combustion is determined by comparing the temperatures measured by upstream temperature sensor 36 and downstream temperature sensor 40 according to equation (1).

The ullage gas samples from first fuel tank 24a and second fuel tank 24b are provided at a constant flow rate so that the mixed ullage gas sample is provided to catalytic reactor 38 at a constant flow rate. The oxygen concentration of the mixed ullage gas sample can be determined as described above. Additionally, control unit 44 can control NEA flow control valve 22 to control the purity or oxygen concentration of the NEA supplied to first and second fuel tanks 24a and 24b such that they remain in an inert state. Alternatively, the oxygen concentration of first and second fuel tanks 24a and 24b can be determined by separate upstream temperature sensors 36, catalytic reactors 38 and downstream temperature sensors 40.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. For example, nitrogen-enriched air can be supplied to fuel tank 24 by a nitrogen generation system using molecular sieve technology or from a NEA storage tank. Therefore, it is intended that the invention not be limited to the particular embodiment(s) disclosed, but that the invention will include all embodiments falling within the scope of the appended claims.

The invention claimed is:

1. A fuel tank inerting system comprising:
   a fuel tank;
   an ullage gas sample outlet located in the fuel tank for removing an ullage gas sample from the fuel tank, the ullage gas sample containing hydrocarbon fuel vapor;
   a catalytic reactor containing a combustion catalyst that supports catalytic combustion of the hydrocarbon fuel vapor, the catalytic reactor connected to the ullage sample outlet;
   a first temperature sensor located upstream with respect to the flow of the ullage gas sample of the catalytic reactor for sensing an upstream temperature of the ullage gas sample;
   a second temperature sensor located downstream with respect to the flow of the ullage gas sample of the catalytic reactor for sensing a downstream temperature of the ullage gas sample; and
   a control unit for comparing the upstream temperature and the downstream temperature of the ullage gas sample to determine the oxygen concentration of the ullage gas sample.

2. The fuel tank inerting system of claim 1, wherein the combustion catalyst includes at least one of $Bi_2MoO_6$ or $Pd/Al_2O_3$.

3. The fuel tank inerting system of claim 1, and further comprising a check arrestor located between the ullage sample outlet and the first temperature sensor.

4. The fuel tank inerting system of claim 1, and further comprising a nitrogen generation system connected to the fuel tank for providing nitrogen-enriched air to the fuel tank.

5. The fuel tank inerting system of claim 4, wherein the control unit adjusts the nitrogen generation system based on a difference between the downstream temperature and the upstream temperature of the ullage gas sample.

6. The fuel tank inerting system of claim 5, wherein the nitrogen generation system further comprises an air separation module to produce the nitrogen-enriched air and a nitrogen-enriched air flow control valve to control the flow of the nitrogen-enriched air into the fuel tank, and wherein the control unit adjusts the nitrogen generation system by actuating the nitrogen-enriched air flow control valve to adjust the purity of the nitrogen-enriched air sent to the fuel tank.

7. The fuel tank inerting system of claim 1, and further comprising:
a second fuel tank; and
a second ullage gas sample outlet located in the second fuel tank for removing a second ullage gas sample from the second fuel tank, wherein the second ullage gas sample is mixed with the ullage gas sample of the fuel tank before the first temperature sensor.

8. The fuel tank inerting system of claim 1, wherein the first temperature sensor is a thermocouple.

9. A method for determining oxygen concentration of a fuel tank, the method comprising:
extracting an ullage gas sample from an ullage of the fuel tank;
directing the ullage gas sample through a catalytic reactor that includes a combustion catalyst that promotes catalytic combustion of hydrocarbon fuel;
measuring an upstream temperature of the ullage gas sample upstream with respect to the flow of the ullage gas sample of the catalytic reactor;
measuring a downstream temperature of the ullage gas sample downstream with respect to the flow of the ullage gas sample of the catalytic reactor; and
comparing the upstream temperature and the downstream temperature of the ullage gas sample to determine the oxygen concentration of the ullage gas sample.

10. The method of claim 9, wherein the combustion catalyst includes at least one of $Bi_2MoO_6$ or $Pd/Al_2O_3$.

11. The method of claim 9, and further comprising:
directing the ullage gas sample through a check arrestor prior to the catalytic reactor.

12. The method of claim 9, and further comprising:
dumping the ullage gas sample overboard after the step of measuring a downstream temperature of the ullage gas sample.

13. A system for measuring oxygen concentration of a gas stream, the system comprising:
a catalytic reactor containing a combustion catalyst that supports the catalytic combustion of hydrocarbon fuel vapor in the gas stream;
a first temperature sensor located upstream with respect to flow of the gas stream of the catalytic reactor for sensing an upstream temperature of the gas stream;
a second temperature sensor located downstream with respect to flow of the gas stream of the catalytic reactor for sensing a downstream temperature of the gas stream; and
a control unit for comparing the upstream temperature and the downstream temperature of the gas stream to determine the oxygen concentration of the gas stream.

14. The system of claim 13, wherein the combustion catalyst includes at least one of $Bi_2MoO_6$ or $Pd/Al_2O_3$.

* * * * *